United States Patent [19]
Eigendorf

[11] Patent Number: 5,259,961
[45] Date of Patent: Nov. 9, 1993

[54] METHOD AND ASSEMBLY FOR THE ON-LINE FLUSHING AND FILLING OF AN EXTRACORPOREAL BLOOD CIRCULATION SYSTEM OF DIALYSIS MACHINES

[75] Inventor: Hans-Günter Eigendorf, Bad Saarow-Pieskow, Fed. Rep. of Germany

[73] Assignee: Medical Support GmbH, Rodgau, Fed. Rep. of Germany

[21] Appl. No.: 892,792

[22] Filed: Jun. 1, 1992

[30] Foreign Application Priority Data

Mar. 13, 1992 [DE] Fed. Rep. of Germany ....... 4208274

[51] Int. Cl.⁵ ............................................. B01D 61/00
[52] U.S. Cl. ................................. 210/646; 210/805; 210/929; 604/4; 604/5
[58] Field of Search ............... 210/645, 646, 805, 806, 210/929; 604/4, 5, 6

[56] References Cited

U.S. PATENT DOCUMENTS

| | | | |
|---|---|---|---|
| 3,669,880 | 6/1972 | Marantz et al. | 210/929 |
| 4,190,047 | 2/1980 | Jacobsen et al. | 210/929 |
| 4,371,385 | 2/1983 | Johnson | 210/929 |
| 4,399,030 | 8/1983 | Hlavinka et al. | 210/929 |
| 4,444,597 | 4/1984 | Gortz et al. | 210/646 |
| 4,834,888 | 5/1989 | Polaschegg | 210/646 |
| 4,844,810 | 7/1989 | Richalley et al. | 210/646 |
| 5,004,548 | 4/1991 | Richalley et al. | 210/646 |
| 5,141,493 | 8/1992 | Jacobsen et al. | 210/646 |
| 5,178,763 | 1/1993 | Delaunay | 210/646 |

Primary Examiner—Robert A. Dawson
Assistant Examiner—Sun Uk Kim
Attorney, Agent, or Firm—Juettner Pyle & Lloyd

[57] ABSTRACT

In the on-line method of the invention, dialysis liquid which has been produced or prepared by a dialysis machine is taken from the dialyzer at the blood side and pumped, either by means of a blood pump of the machine or by the pump of the dialysis liquid circuit, through the blood tubes, optionally using the filling program specific to the machine. As a result, the extracorporeal blood circulation system need no longer be flushed and filled with a salt solution, which has so far entailed considerable costs.

9 Claims, 1 Drawing Sheet

METHOD AND ASSEMBLY FOR THE ON-LINE FLUSHING AND FILLING OF AN EXTRACORPOREAL BLOOD CIRCULATION SYSTEM OF DIALYSIS MACHINES

BACKGROUND OF THE INVENTION

This invention relates to a method for flushing and filling an extracorporeal blood circulation system of dialysis machines, in particular blood tubes and dialyzer, and to an assembly with the aid of which an extracorporeal blood circulation system can be flushed and filled. The filling process includes the deaerating of the extracorporeal blood circulation system, the deaerating operation being an indispensable precondition for a dialysis treatment.

Disposable tubes which are normally packed under sterile conditions and have to be flushed, deaerated and filled prior to a treatment are nowadays used a arterial and venous blood tubes of an extracorporeal blood circulation system. These operations have so far been carried out with physiological salines that are conveyed by the blood pump of the machine through the tube system and the dialyzer to flush the extracorporeal blood circulation system, thereby freeing it from impurities, and to fill the system, so that air is entirely removed.

The use of a saline flushing liquid has the disadvantage that it entails considerable costs.

SUMMARY OF THE INVENTION

It is the object of the present invention to provide a method which is used for flushing, deaerating and filling and extracorporeal blood circulation system of dialysis machines and which is nevertheless inexpensive. It is another object to provide an assembly with which this method can be carried out.

In the method of the invention, the dialysis liquid which has been produced or prepared by the dialysis machine is conveyed through or into the extracorporeal blood circulation system for the purpose of flushing, deaerating and filling. As a result, a saline solution filled into a bag need no longer be provided for this purpose. Moreover, such a bag had to be connected by an operator to the arterial blood tube in former times. Furthermore, saline solutions need no longer be kept available in great amounts for such a purpose, and empty bags need no longer be disposed of.

In accordance with the invention, the dialysis liquid is taken at the blood side of the dialyzer and filtered thereby. This ensures a germ-free state of the flushing and filling liquid in a reliable way, with the dialysis liquid serving as an entirely acceptable substitute for the saline solution.

According to another inventive suggestion, the dialysis liquid taken from the dialyzer can be pumped by the blood pump of the machine through the extracorporeal blood circulation system, which shall be explained in more detail in the following. In this embodiment of the invention, the suction side of the arterial blood tube is preferably connected by means of a disposable article or connector to the dialyzer, preferably at the point to which the venous blood tube is connected during a dialysis treatment. The blood pump segment of the arterial blood tube is inserted into the blood pump of the machine, preferably a roller-type pump, and the other, free end of the arterial blood tube is preferably coupled via another disposable article with the inlet of the venous blood tube. The venous blood tube is passed across an air detector in the conventional way. The other end of the venous blood tube is connected downstream of the dialyzer to the dialysis liquid circuit, preferably by means of another disposable article, to a sampling valve of this dialysis liquid circuit.

When the blood pump is put into operation, dialysis liquid is drawn through the semipermeable membrane of the dialyzer into the blood tubes. Only sterile and germ-free flushing liquid flows into the extracorporeal blood circulation system. The flushing liquid and the air previously existing in the extracorporeal circuit are introduced downstream of the dialyzer machine, whereby disturbances of the equilibrium or other machine faults are avoided.

According to an alternative suggestion of the invention, the dialysis fluid is pumped by a pump of the dialysis liquid circuit, and not by the blood pump of the machine, through or into the blood tubes for the purpose of flushing, deaerating and filling the extracorporeal blood circulation system. This process may be initiated by the filling program of the machine.

To be more specific, in this embodiment of the method of the invention, the arterial and venous blood tubes are coupled to the dialyzer in the same way as during a dialysis treatment. In the dialysis liquid circuit, a three-way valve with 2/2 ports is arranged downstream of the dialyzer for closing the dialysis liquid circuit either fully or partly or for interrupting the same. The third port of this three-way valve which may, e.g. be adjusted mechanically is not positioned in the dialysis liquid circuit and is capable of establishing a connection which is open to the atmosphere. The valve partially or entirely blocks return of the dialysis liquid through its own circuit and causes the liquid to pass through the dialyzer and through the blood tubes.

In a preferred embodiment of the invention, the three-way valve is an electrically operated valve which is controlled by the dialysis apparatus itself or by an additional device.

For flushing and filling the extracorporeal blood circulation system, the three-way valve is operated in such a way that the dialysis liquid circuit is opened to the atmosphere, whilst the line leading away from the dialyzer is closed fully or partly. It should be noted that it is also possible to adjust an intermediate position of the three-way valve in which only part of the dialysis liquid can flow off through the valve assembly. This shall be explained further below.

When the dialysis liquid circuit is open to the atmosphere due to the switching of the three-way valve, the sensor means of the machine can sense the air flowing via the associated connection into the interior of the machine, and initiate the filling program specific to the machine. The dialysis liquid from the machine is pressed via the dialyzer into the two connected blood tubes, since the three-way valve has interrupted the dialysis liquid circuit either fully or partly. The blood tubes are thus flushed, deaerated and filled with the dialysis liquid.

According to another inventive suggestion, the connections at the patient are, e.g., coupled to an empty bag. In this case it might be of advantage to switch the three-way valve to an intermediate position at which the dialysis liquid circuit is closed only partly. As a result, the bag is not filled with an amount of flushing liquid that is too great, and is also not subjected to a pressure that is too great and might make the bag burst.

In an alternative embodiment of the invention, the connections of the two blood tubes at the patient can be coupled to the third connection of the three-way valve which is not positioned within the dialysis liquid circuit, i.e. preferably by means of a suitable disposable article. Another possibility is that the free ends of the blood tubes are arranged such that they terminate in an open vessel.

In this last-mentioned embodiment of the method of the invention and the assembly of the invention, respectively, the arterial pump segment is not inserted into the blood pump because the arterial blood tube is filled in the opposite direction.

An advantage of the above-described second variant is that sterile disposable articles are not needed at the dialyzer side and that the arterial and venous blood tubes are connected in the usual way and need not be varied in any way. the filling program specific to the machine, which program is responsive to air flowing into the interior of the machine.

The assembly of the invention has already been described above to a large extent in connection with the method of the invention. According to an additional inventive suggestion, a sterile filter is arranged upstream of the dialyzer in the dialysis liquid circuit to promote and ensure the necessary germ-free state.

According to another aspect of the invention, the dialysis liquid which is used as a flushing liquid is employed at the end of the dialysis treatment for flushing the extracorporeal blood circulation system. For the is purpose, it is expedient to discharge said liquid during the flushing operation into a bag. A flushing operation is necessary to return all of the blood to the patient after a dialysis treatment. This has so far been accomplished with the air of a saline solution.

According to another inventive suggestion, the extracorporeal components are cleaned such that they can be used again. To this end, an assembly may be chosen as is described further above in connection with the first embodiment of the method of the invention. During a cleaning program specific to the dialysis machine, cleaning liquid is passed due to the conveying action of the blood pump via the semipermeable membrane of the dialyzer into the extracorporeal circuit, with the latter being thereby cleaned.

It is, of course, within the scope of the invention to further use the extracorporeal components as disposable articles.

It will be understood that during dialysis treatment, the blood and dialysis liquid flow in separate paths on either side of the membrane of the dialyzer. During the flushing operation, dialysis liquid is filtered through the membrane and into the blood circulation components.

Other features, advantages and details of the invention will become apparent from the following description of some preferred embodiments taken in conjunction with the drawing, in which there is shown in a purely diagrammatic way.

DESCRIPTION OF THE PREFERRED EMBODIMENTS

Figure 2:
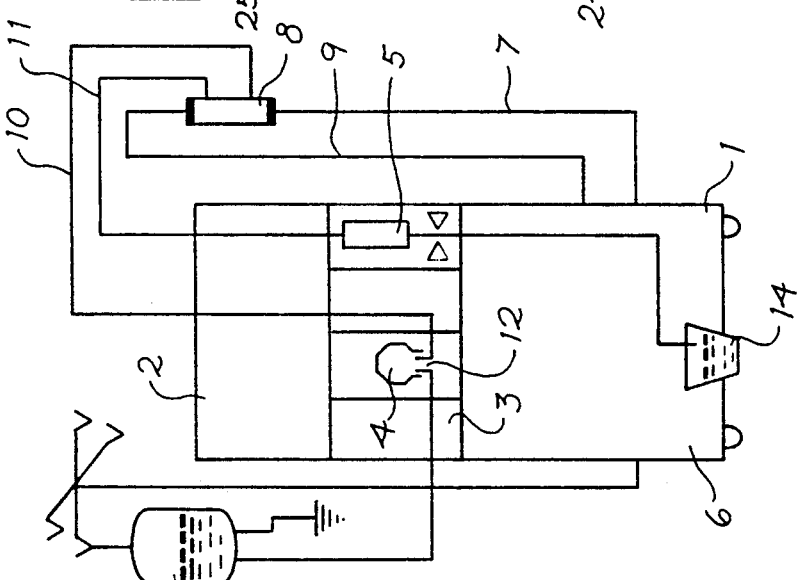
FIG. 2, a conventional assembly.

First of all, reference is made to FIG. 2 to explain conventional methods employed for flushing, dearating and filing an extracorporeal blood circulation system. The figure illustrates a dialysis machine 1 proper having an upper monitoring level 2, a central level 3 comprising a blood pump 4 and an air detector 5, as well as a lower level 6 including the hydraulic part.

Dialysis machine 1 is connected via a supply line 7 to dialyzer 8 from which a return line 9 leads back to dialysis machine 1 to close a dialysis liquid circuit.

An arterial blood tube 10 and a venous blood tube 11 are connected to dialyzer 8 at the illustrated points for carrying out a dialysis treatment. A blood pump segment 12 of the arterial blood tube 10 is inserted into blood pump 4, whilst the venous blood tube 11 is guided via air detector 5.

For the preparation of a dialysis treatment, blood tubes 10 and 11 must be flushed and the extracorporeal blood circulation system must be deaerated and filled. To this end, it has so far been customary to connect the free end of the arterial blood tube 10 to the outlet of a bag 13 containing a salt solution. Blood pump 4 conveys the salt solution through the arterial blood tube 10, dialyzer 8, venous blood tube 11 and air detector 5 to discharge the flushing liquid into an open container 14 in the end.

Figure 3:
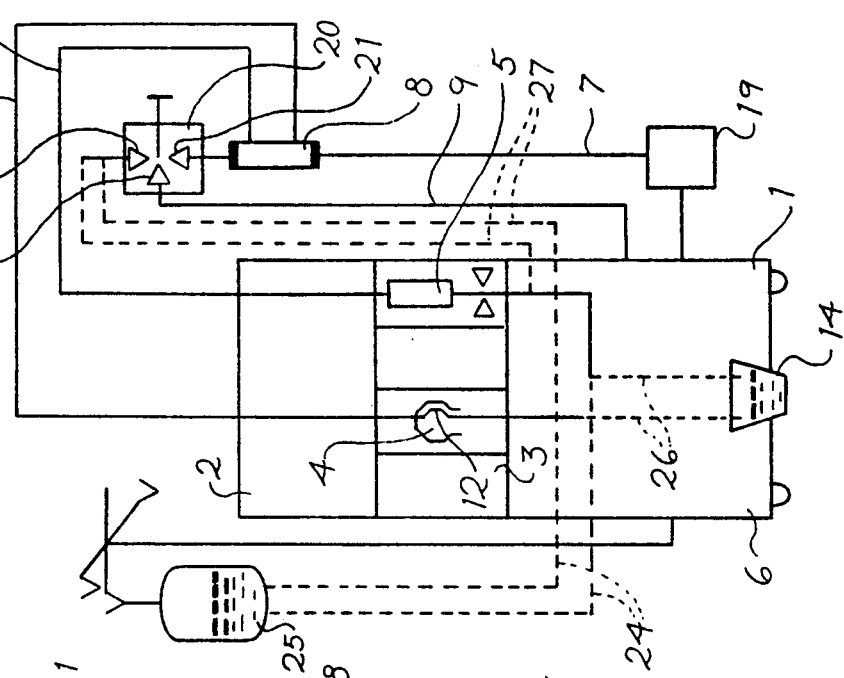
FIG. 3, a second embodiment of the assembly of the invention.
Figure 1:
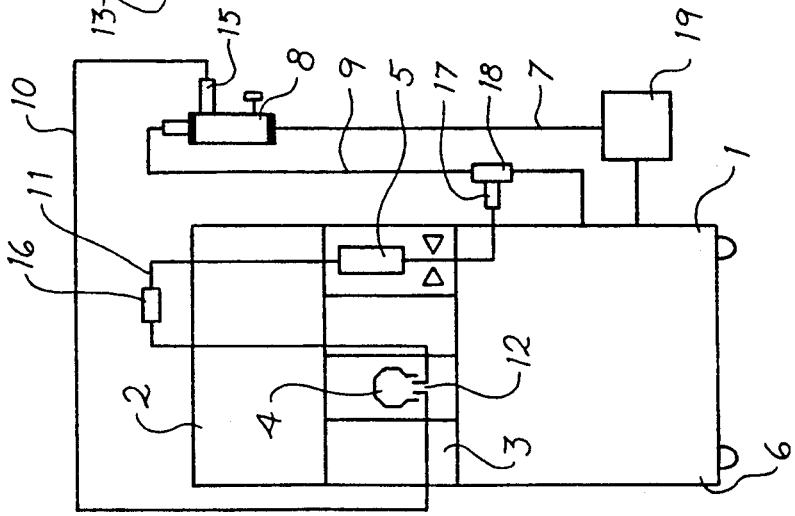
FIG. 1, a first embodiment of the assembly of the invention.

Reference is now made to FIG. 1 in which, just like FIG. 3, the components corresponding to those of FIG. 2 are designated by identical reference numerals. For the sake of clarity, these reference numerals will not be repeated.

In this embodiment of the invention, the arterial blood tube 10 is connected by means of a disposable article 15 to dialyzer 8 at the place to which the venous blood tube 11 is coupled a according to FIG. 2. The blood pump segment 12 of the arterial blood tube 10 is inserted into blood pump 4, and the free end of the tube 10 is connected by means of a disposable article 16 to the venous blood tube 11. The venous blood tube 11, in turn, is guided across air detector 5 and is connected by means of disposable article 17 to a sampling valve 18.

A sterile filter 19 which promotes and ensures the germ-free condition of the flushing liquid is arranged in line 7 of the dialysis liquid circuit.

Dialysis liquid is conveyed by blood pump 4 from the dialysis liquid circuit 7, 8, 9, into the arterial tube 10 and the venous tube 11, from where it is returned into the dialysis liquid circuit (at 18) to avoid disturbances of the equilibrium or other machine faults.

In the embodiment of the invention illustrated in FIG. 3, the arterial blood tube 10 and the venous blood tube 11 are connected to dialyzer 8 in the way as described with reference to FIG. 2 and required during a dialysis treatment. In this embodiment, a three-way valve 20 is arranged in line 9. Connections 21 and 22 of said valve are assigned to line 9, whilst its connection 23 is normally open to the atmosphere.

During a dialysis treatment a connection is established between 21 and 22, whilst, as already stated, connection 23 is open to the atmosphere. For the purpose of flushing the extracorporeal blood circulation system, valve assembly 20 is switched to passage 22, 23. An intermediate position in which there exists a restricted passage 21, 22 can also be selected. Dialysis liquid from dialysis machine 1 is pressed via dialyzer 8 into blood tubes 10, 11, with the latter being flushed. Flushing liquid may be discharged either via lines 24 into a bag 25 or via lines 26 into an open vessel 14 or may be supplied via lines 27 to connection 23 of three-way valve 20, from where liquid is passed into the dialysis liquid circuit or rather line 9 thereof.

The blood pump segment is not inserted into blood pump 4 in this embodiment.

I claim:

1. A method for flushing and filling of an extracorporeal blood circulation system of a dialysis machine, said machine having a dialyzer, a separate dialysis liquid circuit flowing through one side of the dialyzer, with the extracorporeal blood circulation system flowing through the other side of the dialyzer for removal of impurities from the blood, said method comprising the steps of transporting dialysis liquid from the dialysis liquid circuit into and through the extracorporeal blood circulation system to flush and fill said system, and conducting a dialysis treatment.

2. The method according to claim 1, wherein dialysis liquid is passed through said dialyzer and is thereby filtered.

3. The method according to claim 1, wherein said dialysis machine has a blood pump and wherein dialysis liquid is pumped by said blood pump into said extracorporeal blood circulation system.

4. The method according to claim 1, wherein the dialysis liquid circuit comprises a pump, and wherein the dialysis liquid is pumped by said pump into said extracorporeal blood circulation system.

5. The method according to claim 1, wherein said dialysis machine has a filling program for filling the dialysis circuit, and wherein the step of transporting dialysis liquid through the extracorporeal blood circulation system is initiated by said filling program.

6. The method of claim 1 additionally comprising the step of passing the dialysis liquid through a filter prior to passage through the dialyzer.

7. The method of claim 1 wherein the blood circulation system is flushed and filled prior to the dialysis treatment.

8. The method of claim 1 wherein the blood circulation system is flushed and filled after completion of the dialysis treatment.

9. A method of flushing the extracorporeal blood circulation circuit of a dialysis machine, said machine comprising a dialyzer with the blood circulation circuit passing through one side of the dialyzer, and a dialysis liquid circuit containing dialysis liquid passing through the other side of the dialyzer, said method comprising the steps of pumping dialysis liquid from the dialysis liquid circuit through the dialyzer and into the blood circuit with said dialysis liquid.

* * * * *